United States Patent
Morita et al.

(10) Patent No.: US 9,796,862 B2
(45) Date of Patent: Oct. 24, 2017

(54) ACTIVE-ENERGY-RAY-CURABLE COMPOSITION, ACTIVE-ENERGY-RAY-CURABLE INK, INK STORED CONTAINER, INK EJECTING DEVICE, METHOD FOR FORMING IMAGE, AND IMAGE

(71) Applicants: Mitsunobu Morita, Shizuoka (JP); Soh Noguchi, Kanagawa (JP)

(72) Inventors: Mitsunobu Morita, Shizuoka (JP); Soh Noguchi, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/155,229

(22) Filed: May 16, 2016

(65) Prior Publication Data
US 2016/0347960 A1 Dec. 1, 2016

(30) Foreign Application Priority Data

May 27, 2015 (JP) .................. 2015-107105
Mar. 14, 2016 (JP) .................. 2016-049823

(51) Int. Cl.
*C09D 11/101* (2014.01)
*C09D 11/322* (2014.01)
(Continued)

(52) U.S. Cl.
CPC ............ *C09D 11/101* (2013.01); *C07C 69/73* (2013.01); *C07C 255/38* (2013.01);
(Continued)

(58) Field of Classification Search
CPC ................ C09D 11/101; C07C 57/30
See application file for complete search history.

(56) References Cited

U.S. PATENT DOCUMENTS 8,632,174 B2    1/2014 Noguchi et al.
8,727,522 B2    5/2014 Maekawa et al.
(Continued)

FOREIGN PATENT DOCUMENTS

JP    07295221 A * 11/1995
JP    2006-299094    11/2006
(Continued)

OTHER PUBLICATIONS

Manickum and Roos (S. Afr. J. Chem., 1994, 47(1), 1-16).*

*Primary Examiner* — Vu A Nguyen
(74) *Attorney, Agent, or Firm* — Oblon, McClelland, Maier & Neustadt, L.L.P.

(57) ABSTRACT

To provide an active-energy-ray-curable composition including: a (meth)acrylic acid ester compound represented by General Formula (1) below,

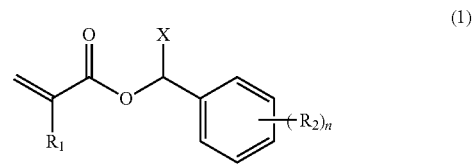
(1)

where in the General Formula (1), $R_1$ represents a hydrogen atom or a methyl group, $R_2$ represents a hydrogen atom, an alkyl group having from 1 through 5 carbon atoms, or an alkyloxy group having from 1 through 5 carbon atoms, n is an integer of from 0 through 5, and X represents an electron-withdrawing functional group.

13 Claims, 3 Drawing Sheets

(51) Int. Cl.
- *C07C 69/73* (2006.01)
- *C07C 255/38* (2006.01)
- *B33Y 10/00* (2015.01)
- *B33Y 70/00* (2015.01)
- *B33Y 80/00* (2015.01)
- *B33Y 30/00* (2015.01)

(52) U.S. Cl.
CPC .............. *C09D 11/322* (2013.01); *B33Y 10/00* (2014.12); *B33Y 30/00* (2014.12); *B33Y 70/00* (2014.12); *B33Y 80/00* (2014.12)

(56) References Cited

U.S. PATENT DOCUMENTS

| | | |
|---|---|---|
| 8,815,140 B2 | 8/2014 | Aruga et al. |
| 8,871,861 B2 | 10/2014 | Shoshi et al. |
| 9,267,043 B2 | 2/2016 | Morita et al. |
| 2011/0060100 A1 | 3/2011 | Kimura et al. |
| 2012/0147103 A1 | 6/2012 | Hasegawa et al. |
| 2012/0242768 A1 | 9/2012 | Seno et al. |
| 2013/0144057 A1 | 6/2013 | Morita |
| 2013/0267625 A1 | 10/2013 | Noguchi et al. |
| 2014/0045965 A1 | 2/2014 | Noguchi et al. |
| 2014/0363634 A1 | 12/2014 | Morita et al. |
| 2016/0075894 A1 | 3/2016 | Noguchi et al. |

FOREIGN PATENT DOCUMENTS

| | | |
|---|---|---|
| JP | 2007-056232 | 3/2007 |
| JP | 2013-256487 | 12/2013 |

\* cited by examiner

ACTIVE-ENERGY-RAY-CURABLE COMPOSITION, ACTIVE-ENERGY-RAY-CURABLE INK, INK STORED CONTAINER, INK EJECTING DEVICE, METHOD FOR FORMING IMAGE, AND IMAGE

CROSS-REFERENCE TO RELATED APPLICATIONS

The present application claims priority under 35 U.S.C. §119 to Japanese Patent Application No. 2015-107105, filed May 27, 2015 and Japanese Patent Application No. 2016-049823, filed Mar. 14, 2016. The contents of which are incorporated herein by reference in their entirety.

BACKGROUND OF THE INVENTION

Field of the Invention

The present disclosure relates to active-energy-ray-curable compositions, active-energy-ray-curable inks, ink stored containers, ink ejecting devices, methods for forming images, and images.

Description of the Related Art

An inkjet recording system is known as a method for forming an image on recording medium such as paper. This inkjet recording system has high consumption efficiency of an ink, and is excellent in property of saving resources. In addition, the inkjet recording system can reduce the cost of ink necessary to form an image.

Recently, there is a need for an inkjet recording system using an active-energy-ray-curable ink. For example, proposed are a (meth)acrylate compound having an urethane structure as a polar group, or having a core structure obtained by combining a cyclic structure containing a hetero atom with a urethane structure; and an active-energy-ray-curable composition containing the (meth)acrylate compound (see Japanese Unexamined Patent Application Publication No. 2013-256487).

Moreover, proposed is an ink composition containing a polymerizable compound that contains a carboxyl group as a polar group in a molecular of the polymerizable compound (see Japanese Unexamined Patent Application Publication No. 2006-299094).

In addition, proposed is an ink composition for inkjet, which is obtained by combining phenoxyethyl acrylate, vinylcaprolactam, and 2-hydroxy-3-phenoxypropylacrylate containing a hydroxyl group (see Japanese Unexamined Patent Application Publication No. 2007-56232).

SUMMARY OF THE INVENTION

An active-energy-ray-curable composition of the present disclosure includes a (meth)acrylic acid ester compound represented by General Formula (1) below.

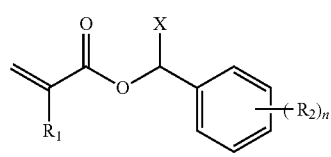

(1)

Here, in the General Formula (1), $R_1$ represents a hydrogen atom or a methyl group. $R_2$ represents a hydrogen atom, an alkyl group having from 1 through 5 carbon atoms, or an alkyloxy group having from 1 through 5 carbon atoms. n is an integer of from 0 through 5. X represents an electron-withdrawing functional group.

DESCRIPTION OF THE EMBODIMENTS (Active-Energy-Ray-Curable Composition)

Figure 1:
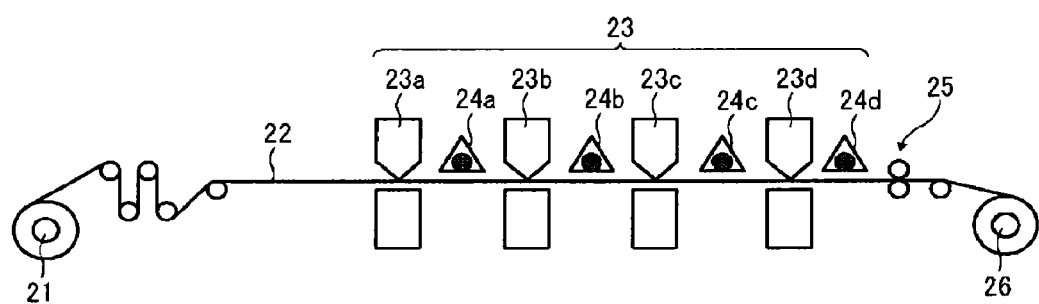
FIG. 1 is a schematic view of an example of an image forming apparatus of the present disclosure.

An active-energy-ray-curable composition of the present disclosure contains a (meth)acrylic acid ester compound represented by General Formula (1) below, and further contains other components if necessary.

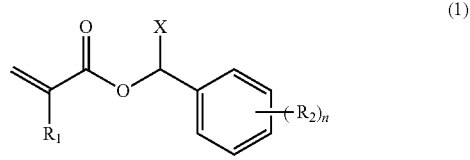

(1)

Here, in the General Formula (1), $R_1$ represents a hydrogen atom or a methyl group. $R_2$ represents a hydrogen atom, an alkyl group having from 1 through 5 carbon atoms, or an alkyloxy group having from 1 through 5 carbon atoms. n is an integer of from 0 through 5. X represents an electron-withdrawing functional group.

The present disclosure has an object to provide an active-energy-ray-curable composition that has little odor and is excellent in photopolymerizing ability and photocurability.

According to the present disclosure, an active-energy-ray-curable composition that has little odor and is excellent in photopolymerizing ability and photocurability can be provided.

In the General Formula (1), examples of the electron-withdrawing functional group represented by X include a structure containing a carbonyl group (carbonyl-group-containing structure), a cyano group, and a halogen atom. Among them, a carbonyl-group-containing structure is preferable because electron-withdrawing ability of the carbonyl-group-containing structure is between the cyano group high in electron-withdrawing ability and the halogen atom low in electron-withdrawing ability, and polarity of the monomer represented by the carbonyl-group-containing structure is excellent in compatibility with components such as a polymerization initiator.

Examples of the carbonyl-group-containing structure include an ester group, a ketone group, a formyl group, an amide group, and a carboxyl group.

In the General Formula (1), $R_2$ represents a hydrogen atom, an alkyl group having from 1 through 5 carbon atoms, or an alkyloxy group having from 1 through 5 carbon atoms.

Examples of the alkyl group include a methyl group, an ethyl group, and a propyl group.

Examples of the alkyloxy group include a methoxy group, an ethoxy group, and a propoxy group.

n is an integer of from 0 through 5, and is preferably 0.

A compound represented by the General Formula (1) is a monofunctional (meth)acrylic acid ester compound having a benzene-ring-containing structure as a core structure, and has an aprotic polar structure branched from the core structure. The monofunctional (meth)acrylic acid ester compound cannot form a cross-linked structure as polymerization reaction proceeds. Therefore, compared to the multifunctional (meth)acrylic acid ester compounds, it is difficult for the monofunctional (meth)acrylic acid ester compounds to be solidified, which leads to poor curing ability of the monofunctional (meth)acrylic acid ester compounds. When a cyclic structure is introduced to the monofunctional (meth)acrylic acid ester compound in a molecular structure, a glass transition temperature (Tg) of the cured product becomes high, and is easily solidified.

The (meth)acrylic acid ester compound represented by the General Formula (1) contains a benzene ring as a cyclic structure, and contains an aprotic polar group having electron-withdrawing ability as a branched structure. It is believed that this branched aprotic polar group attracts (meth)acrylic acid ester compounds to each other, which leads to facilitation of polymerization reaction. In addition, it is believed that, in a cured product of the (meth)acrylic acid ester compound after polymerization reaction, interaction generated by the polar groups improves the cured product in hardness. The aprotic polar group appropriately prevents intermolecular interaction, and thus viscosity of the active-energy-ray-curable composition does not drastically rise. These properties are suitable for the active-energy-ray-curable composition.

As described above, the (meth)acrylic acid ester compound obtained by combining an aromatic cyclic structure and an aprotic polar group introduced to the (meth)acrylic acid ester compound as a branched structure can improve functions of the active-energy-ray-curable composition. As a result, the active-energy-ray-curable composition containing the compound represented by the General Formula (1) is considerably high in curing ability, and can be cured through low energy.

The compound represented by the General Formula (1) is preferably a compound represented by General Formula (2) below.

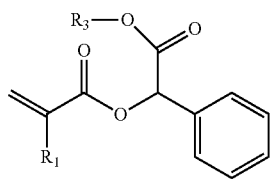

(2)

Here, in the General Formula (2), $R_1$ represents a hydrogen atom or a methyl group. $R_3$ represents a group selected from the group consisting of an aliphatic hydrocarbon group having from 1 through 10 carbon atoms, an alicyclic hydrocarbon group, and an aromatic hydrocarbon group.

$R^3$ in the General Formula (2) is preferably an alkyl group having from 1 through 3 carbon atoms.

The compound represented by the General Formula (2) is preferably a compound represented by General Formula (3) below.

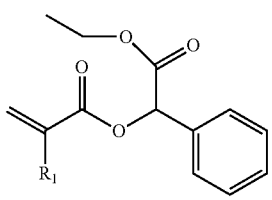

(3)

Here, in the General Formula (3), $R_1$ represents a hydrogen atom or a methyl group.

$R_1$ in the General Formula (3) is preferably a hydrogen atom.

Next, specific examples of the compound represented by the General Formula (1) will be described below, but are not limited thereto. Note that, $R_1$ in these examples has the same meaning as defined above.

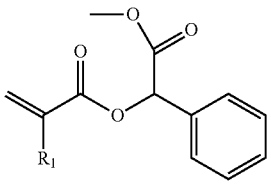

1-1

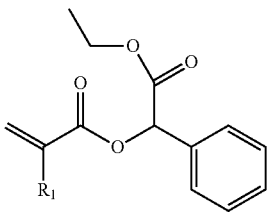

1-2

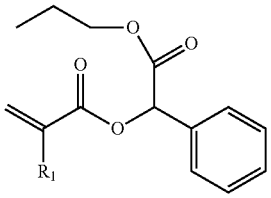

1-3

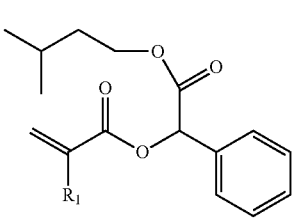

1-4

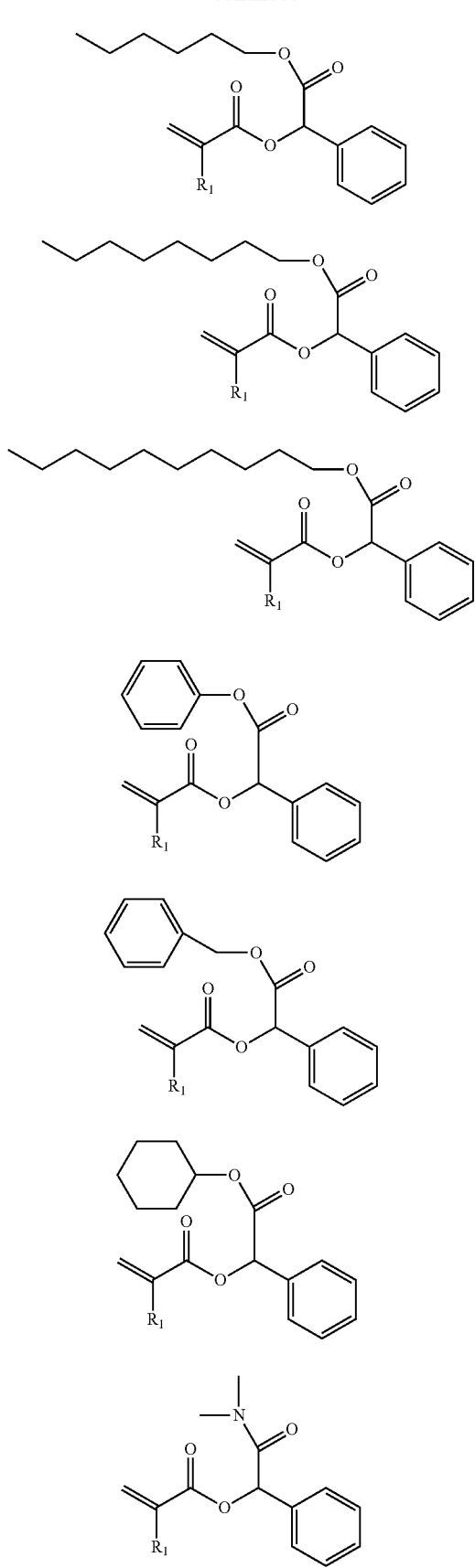
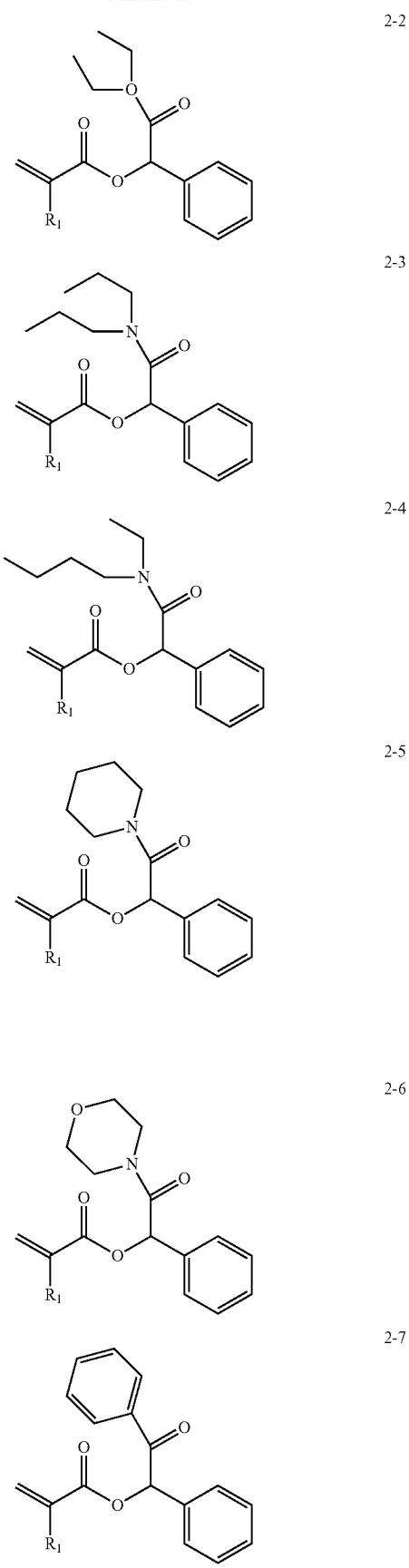

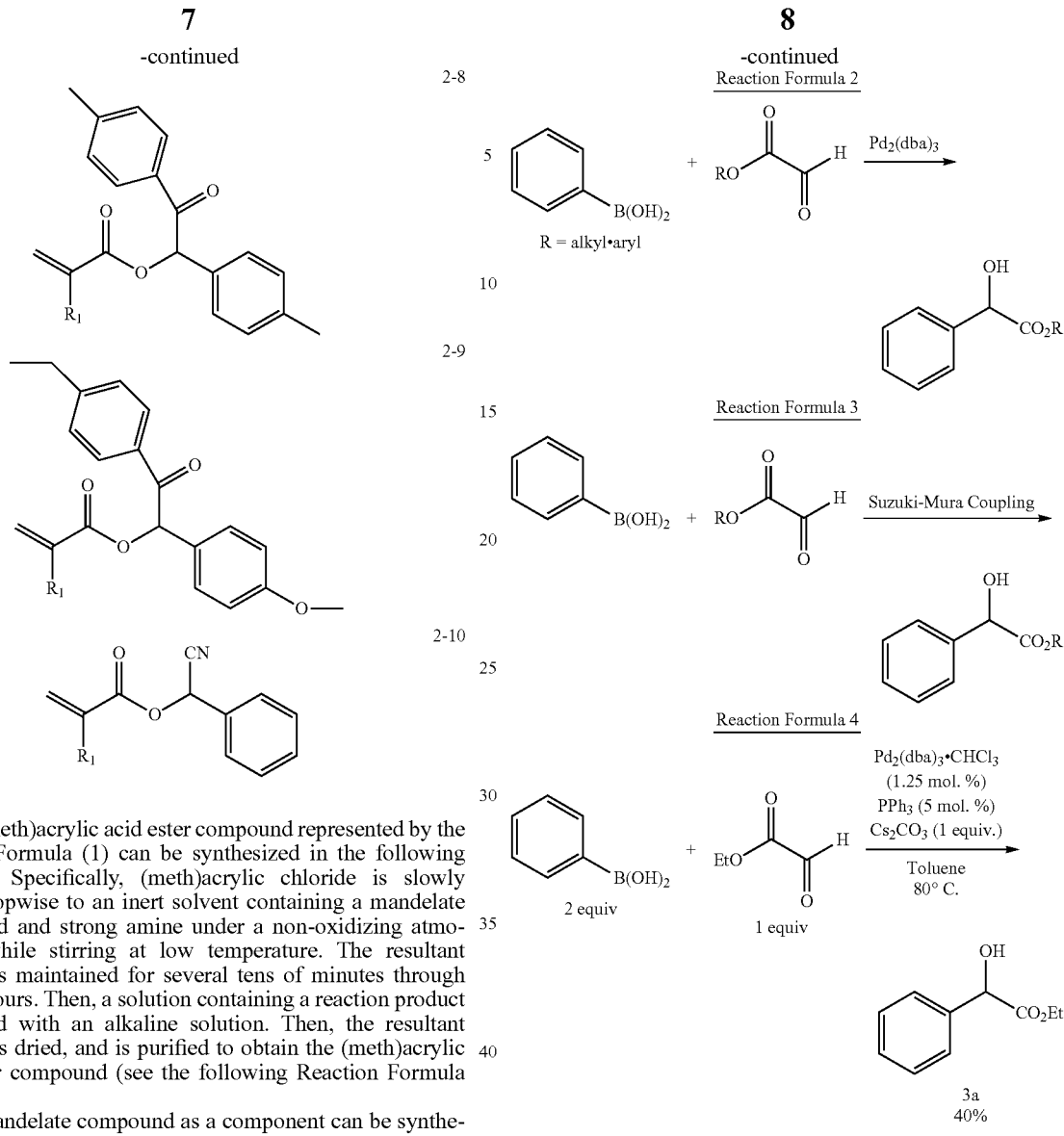

The (meth)acrylic acid ester compound represented by the General Formula (1) can be synthesized in the following manners. Specifically, (meth)acrylic chloride is slowly added dropwise to an inert solvent containing a mandelate compound and strong amine under a non-oxidizing atmosphere while stirring at low temperature. The resultant mixture is maintained for several tens of minutes through several hours. Then, a solution containing a reaction product is washed with an alkaline solution. Then, the resultant solution is dried, and is purified to obtain the (meth)acrylic acid ester compound (see the following Reaction Formula 1).

The mandelate compound as a component can be synthesized by reacting allylboronic acid with alkyl-glyoxalate or aryl-glyoxalate in the presence of a palladium catalyst according to the method for synthesizing madelate disclosed in *Eur. J. Org. Chem.* 2008, 5692-5695 (see the following Reaction Formula 2). Alternatively, the mandelate compound can be synthesized according to the Suzuki-Miura Coupling reaction (see the following Reaction Formula 3). For example, ethyl mandelate can be synthesized according to the following Reaction Formula 4.

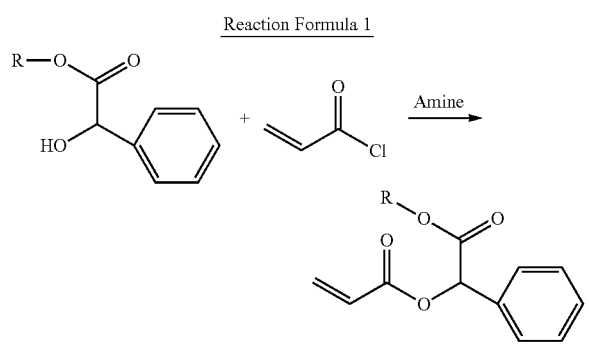

In the above Reaction Formulas, Et represents an ethyl group.

A commercially available product of the mandelate may be used for the component. For example, methyl mandelate is described above. Commercially available products can be used as mandelonitrile containing a cyano group, which is another mandelate component.

Two or more different (meth)acrylic acid ester compounds represented by the General Formula (1) can be mixed in use. In this case, the two or more different (meth)acrylic acid ester compounds include (meth)acrylic acid ester compounds having structural isomers. Note that, a mixing ratio of the compounds is not particularly limited.

An amount of the (meth)acrylic acid ester compound represented by the General Formula (1) is preferably 20% by mass or more but 98% by mass or less, more preferably 30% by mass or more but 90% by mass or less, still more preferably 30% by mass or more but 80% by mass or less, relative to the total amount of the active-energy-ray-curable composition.

<Other Components>

Examples of the other components include polymerization initiators, colorants, polymerizable compounds other than the (meth)acrylic acid ester compounds represented by the General Formula (1), sensitizers, cosensitizers, polymerization inhibitors, solvents, surfactants, leveling additives, matting agents, polyester resins for adjusting membrane property, polyurethane resins, vinyl resins, acrylic resins, rubber resins, waxes, and tackifiers. These may be used alone or in combination thereof.

—Polymerization Initiator—

It is preferable that the active-energy-ray-curable composition further contain a polymerization initiator.

Examples of the polymerization initiator include photoradical polymerization initiators, cationic photopolymerization initiators (photoacid-generating agents), and anionic photopolymerization initiators (photobase-generating agents). These may be used alone or in combination thereof. Among them, photoradical polymerization initiators and anionic photopolymerization initiators are preferable, photoradical polymerization initiators are more preferable. The photopolymerization initiator means a compound that generates polymerization-initiating species by absorbing active energy rays.

The photoradical polymerization initiators are not particularly limited and may be appropriately selected depending on the intended purpose. Examples of the photoradical polymerization initiators include aromatic ketones, acylphosphine oxide compounds, aromatic onium salt compounds, organic peroxides, thio compounds, hexaarylbiimidazole compounds, ketoxime ester compounds, borate compounds, azinium compounds, metallocene compounds, active ester compounds, compounds containing a carbon-halogen bond, and alkylamine compounds.

Examples of the photoradical polymerization initiators include benzophenone, Michler's ketone, 4,4'-bis(diethylamino)benzophenone, xanthone, thioxanthone, isopropylxanthone, 2,4-diethylthio xanthone, 2-ethylanthraquinone, acetophenone, 2-hydroxy-2-methylpropiophenone, 2-hydroxy-2-methyl-4'-isopropylpropiophenone, 1-hydroxycyclohexyl phenyl ketone, isopropyl benzoin ether, isobutyl benzoin ether, 2,2-diethoxyacetophenone, 2,2-dimethoxy-2-phenylacetophenone, camphorquinone, benzanthrone, 2-methyl-1-[4-(methylthio)phenyl]-2-morpholinopropan-1-one, ethyl 2-benzil-2-dimethylamino-1-(4-morpholinophenyl)butanone-1, 4-dimethylaminobenzoate, isoamyl 4-dimethylaminobenzoate, 4,4'-di(t-butylperoxycarbonyl)benzophenone, 3,4,4'-tri(t-butylperoxycarbonyl) benzophenone, 3,3',4,4'-tetra(t-butylperoxycarbonyl) benzophenone, 3,3',4,4'-tetra(t-hexylperoxycarbonyl) benzophenone, 3,3'-di(methoxycarbonyl)-4,4'-bis(t-butylperoxycarbonyl)benzophenone, 3,4'-bis (methoxycarbonyl)-4,3'-bis(t-butylperoxycarbonyl) benzophenone, 4,4'-bis(methoxycarbonyl)-3,3'-bis(t-butylperoxycarbonyl)benzophenone, 1,2-octanedion, 1-[4-(phenylthio)phenyl]-2-(o-benzoyloxime), 2-(4'-methoxystyryl)-4,6-bis(trichloromethyl)-s-triazine, 2-(3',4'-dimethoxystyryl)-4,6-bis(trichloromethyl)-s-triazine, 2-(2',4'-dimethoxystyryl)-4,6-bis(trichloromethyl)-s-triazine, 2-(2'-methoxystyryl)-4,6-bis(trichloromethyl)-s-triazine, 2-(4'-pentyloxystyryl)-4,6-bis(trichloromethyl)-s-triazine, 4-[p-N,N-di(ethoxycarbonylmethyl)]-2,6-di(trichloromethyl)-s-triazine, 1,3-bis(trichloromethyl)-5-(2'-chlorophenyl)-s-triazine, 1,3-bis(trichloromethyl)-5-(4'-methoxyphenyl)-s-triazine, 2-(p-dimethylaminostyryl)benzoxazole, 2-(p-dimethylaminostyryl)benzothiazole, 2-mercaptobenzothiazole, 3,3'-carbonylbis(7-diethylaminocoumarin), 2-(o-chlorophenyl)-4,4',5,5'-tetraphenyl-1,2'-biimidazole, 2,2'-bis(2-chlorophenyl)-4,4',5,5'-tetrakis(4-ethoxycarbonylphenyl)-1,2'-biimidazole, 2,2'-bis(2,4-dichlorophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-trichlorophenyl)-4,4',5,5'-tetraphenyl-1,2'-biimidazole, 3-(2-methyl-2-dimethylaminopropionyl)carbazole, 3,6-bis(2-methyl-2-morpholinopropionyl)-9-n-dodecylcarbazole, 1-hydroxycyclohexyl phenyl ketone, bis($\eta$5-2,4-cyclopentadien-1-yl)-bis[2,6-difluoro-3-(1H-pyrrol-1-yl)phenyl]titanium, bis(2,4,6-trimethylbenzoyl)phenylphosphine oxide, and 2,4,6-trimethylbenzoyldiphenylphosphine oxide. These may be used alone or in combination thereof.

Among them, bis(2,4,6-trimethylbenzoy)phenylphosphine oxide (IRGACURE 819), 2,4,6-trimethylbenzoyldiphenylphosphine oxide (DAROCUR TPO), 1-hydroxycyclohexyl phenyl ketone (IRGACURE 184), 2-methyl-1-[4-(methylthio)phenyl]-2-morpholinopropan-1-one (IRGACURE 907), and 2-dimethylamino-2-(4-methylbenzil)-1-(4-morpholin-4-ylphenyl)butan-1-one (IRGACURE 379) (available from BASF Japan Ltd.) are preferable because the above photoradical polymerization initiators can be considerably dissolved in other components in the active-energy-ray-curable composition, and can cure an ink through a slight irradiation dose of active energy rays.

Examples of the cationic photopolymerization initiators include salts of $B(C_6F_5)_4^-$, $PF_6^-$, $AsF_6^-$, $SbF_6^-$, and $CF_3SO_3^-$ of aromatic onium compounds (e.g., diazonium, ammonium, iodonium, sulfonium, and phosphonium); sulfonated compounds that can generate sulfonic acid; halogenated compound that can generate hydrogen halogenide; and iron allene complexes. These may be used alone or in combination thereof.

Examples of the anionic photopolymerization initiators include o-nitrobenzyl carbamate derivatives, o-acyloxyl derivatives, and o-carbamoyloxime amidine derivatives. These may be used alone or in combination thereof.

—Colorant—

The active-energy-ray-curable composition of the present disclosure may further contain a colorant, and the active-energy-ray-curable composition containing a colorant can form a colored image. Needless to say, the active-energy-ray-curable composition of the present disclosure may not contain the colorant.

The colorant is not particularly limited and may be appropriately selected depending on the intended purpose. Examples of the colorant include pigments, oil-soluble dyes, water-soluble dyes, and disperse dyes. These may be used alone or in combination thereof. Among them, pigments and oil-soluble dyes are preferable, pigments are more preferable in terms of weather resistance and color reproducibility. When the active-energy-ray-curable composition contains the colorant, a colored image can be formed.

Note that, it is preferable that the colorant be a compound that does not serve as a polymerization inhibitor in order that sensitivity of photopolymerization reaction through active energy rays is not deteriorated.

Examples of the pigments include red pigments, magenta pigments, blue pigments, cyan pigments, green pigments, yellow pigments, black pigments, and white pigments. These may be used alone or in combination thereof.

Examples of the red pigments and the magenta pigments include: Pigment Red series (3, 5, 19, 22, 31, 38, 43, 48:1, 48:2, 48:3, 48:4, 48:5, 49:1, 53:1, 57:1, 57:2, 58:4, 63:1, 81, 81:1, 81:2, 81:3, 81:4, 88, 104, 108, 112, 122, 123, 144, 146, 149, 166, 168, 169, 170, 177, 178, 179, 184, 185, 208, 216, 226, and 257); Pigment Violet series (3, 19, 23, 29, 30, 37, 50, and 88); and Pigment Orange series (13, 16, 20, and 36). These may be used alone or in combination thereof.

Examples of the blue pigments and the cyan pigments include Pigment Blue series (1, 15, 15:1, 15:2, 15:3, 15:4, 15:6, 16, 17-1, 22, 27, 28, 29, 36, and 60). These may be used alone or in combination thereof.

Examples of the green pigments include Pigment Green series (7, 26, 36, and 50). These may be used alone or in combination thereof.

Examples of the yellow pigments include Pigment Yellow series (1, 3, 12, 13, 14, 17, 34, 35, 37, 55, 74, 81, 83, 93, 94, 95, 97, 108, 109, 110, 137, 138, 139, 153, 154, 155, 157, 166, 167, 168, 180, 185, and 193). These may be used alone or in combination thereof.

Examples of the black pigments include Pigment Black series (7, 28, and 26). These may be used alone or in combination thereof.

Examples of the white pigments include Pigment White series (6, 18, and 21). These may be used alone or in combination thereof.

Examples of the oil-soluble dyes include yellow oil-soluble dyes, magenta oil-soluble dyes, and cyan oil-soluble dyes. These may be used alone or in combination thereof.

Examples of the yellow oil-soluble dyes include: as a coupling agent, aryl or heteryl azo dyes containing phenols, naphthols, anilines, pyrazolones, pyridines, and open-chain active methylene compounds; and as a coupling agent, methine dyes (e.g., benzylidene dyes, monomethine oxonol dyes, and azomethine dyes containing an open-chain-active-compound, quinone dyes (e.g., naphthoquinone dyes and anthraquinone dyes); quinophthanone dyes, nitro-nitroso dyes, acridine dyes, and acridinone dyes. These may be used alone or in combination thereof.

Examples of the magenta oil-soluble dyes include: as a coupling agent, aryl or heteryl azo dyes containing phenols, naphthols, and anilines; and as a coupling agent, azomethine dyes containing pyrazolones and pyrazolotriazoles; methine dyes (e.g., arylidene dyes, styryl dyes, merocyanine dyes, and oxonol dyes), carbonium dyes (e.g., diphenylmethane dyes, triphenylmethane dyes, and xanthene dyes), quinone dyes (e.g., naphthoquinone, anthraquinone, and anthrapyridone), and polycyclic dyes (e.g., dioxane dyes). These may be used alone or in combination thereof.

Examples of the cyan oil-soluble dyes include: indoaniline dyes; indophenol dyes; as a coupling agent, polymethine dyes (e.g., cyanine dyes, oxonol dyes, merocyanine dyes, and azomethine dyes containing pyrrolotriazole), carbonium dyes (e.g., diphenylmethane dyes, triphenylmethane dyes, and xanthene dyes), phthalocyanine dyes, and anthraquinone dyes; and as a coupling agent, aryl or heteryl azo dyes containing phenols, naphthols, and anilines, and indigo•thioindigo dyes. These may be used alone or in combination thereof.

Specific examples of the oil-soluble dyes include: C. I. Solvent Black series (3, 7, 27, 29, and 34); C. I. Solvent•Yellow series (14, 16, 19, 29, 30, 56, 82, 93, and 162); C. I. Solvent•Red series (1, 3, 8, 18, 24, 27, 43, 49, 51, 72, 73, 109, 122, 132, and 218); C. I. Solvent•Violet 3; C. I. Solvent Blue series (2, 11, 25, 35, 38, 67, and 70); C. I. Solvent•Green series (3 and 7); and C. I. Solvent•Orange 2. These may be used alone or in combination thereof.

Examples of the water-soluble dyes include dyes classified based on the color index, such as acid dyes, direct dyes, basic dyes, reactive dyes, and food dyes.

Examples of the acid dyes and the food dyes include: C. I. Acid Yellow series (17, 23, 42, 44, 79, and 142); C. I. Acid Red series (1, 8, 13, 14, 18, 26, 27, 35, 37, 42, 52, 82, 87, 89, 92, 97, 106, 111, 114, 115, 134, 186, 249, 254, and 289); C. I. Acid Blue series (9, 29, 45, 92, and 249); C. I. Acid Black series (1, 2, 7, 24, 26, and 94); C. I. Food Yellow series (3 and 4); C. I. Food Red series (7, 9, and 14); and C. I. Food Black series (1 and 2). These may be used alone or in combination thereof.

Examples of the direct dyes include: C. I. Direct Yellow series (1, 12, 24, 26, 33, 44, 50, 86, 120, 132, 142, and 144); C. I. Direct Red series (1, 4, 9, 13, 17, 20, 28, 31, 39, 80, 81, 83, 89, 225, and 227); C. I. Direct Orange series (26, 29, 62, and 102); C. I. Direct Blue series (1, 2, 6, 15, 22, 25, 71, 76, 79, 86, 87, 90, 98, 163, 165, 199, and 202); and C. I. Direct Black series (19, 22, 32, 38, 51, 56, 71, 74, 75, 77, 154, 168, and 171). These may be used alone or in combination thereof.

Examples of the basic dyes include: C. I. Basic Yellow series (1, 2, 11, 13, 14, 15, 19, 21, 23, 24, 25, 28, 29, 32, 36, 40, 41, 45, 49, 51, 53, 63, 64, 65, 67, 70, 73, 77, 87, and 91); C. I. Basic Red series (2, 12, 13, 14, 15, 18, 22, 23, 24, 27, 29, 35, 36, 38, 39, 46, 49, 51, 52, 54, 59, 68, 69, 70, 73, 78, 82, 102, 104, 109, and 112); C. I. Basic Blue series (1, 3, 5, 7, 9, 21, 22, 26, 35, 41, 45, 47, 54, 62, 65, 66, 67, 69, 75, 77, 78, 89, 92, 93, 105, 117, 120, 122, 124, 129, 137, 141, 147, and 155); and C. I. Basic Black series (2 and 8). These may be used alone or in combination thereof.

Examples of the reactive dyes include: C. I. Reactive Black series (3, 4, 7, 11, 12, and 17); C. I. Reactive Yellow series (1, 5, 11, 13, 14, 20, 21, 22, 25, 40, 47, 51, 55, 65, and 67); C. I. Reactive Red series (1, 14, 17, 25, 26, 32, 37, 44, 46, 55, 60, 66, 74, 79, 96, and 97); and C. I. Reactive Blue series (1, 2, 7, 14, 15, 23, 32, 35, 38, 41, 63, 80, and 95). These may be used alone or in combination thereof.

Examples of the disperse dyes include: C. I. Disperse Yellow series (5, 42, 54, 64, 79, 82, 83, 93, 99, 100, 119, 122, 124, 126, 160, 184:1, 186, 198, 199, 201, 204, 224, and 237); C. I. Disperse Orange series (13, 29, 31:1, 33, 49, 54, 55, 66, 73, 118, 119, and 163); C. I. Disperse Red series (54, 60, 72, 73, 86, 88, 91, 92, 93, 111, 126, 127, 134, 135, 143, 145, 152, 153, 154, 159, 164, 167:1, 177, 181, 204, 206, 207, 221, 239, 240, 258, 277, 278, 283, 311, 323, 343, 348, 356, and 362); C. I. Disperse Violet 33, C. I. Disperse Blue series (56, 60, 73, 87, 113, 128, 143, 148, 154, 158, 165, 165:1, 165:2, 176, 183, 185, 197, 198, 201, 214, 224, 225, 257, 266, 267, 287, 354, 358, 365, and 368); and C. I. Disperse Green series (6:1 and 9). These may be used alone or in combination thereof.

It is preferable that the pigment be appropriately dispersed in the active-energy-ray-curable composition. Examples of the dispersing include methods for dispersing the pigment using a dispersing device and methods for dispersing the pigment by the addition of a dispersing agent.

The dispersing device is not particularly limited and may be appropriately selected depending on the intended purpose. Examples of the dispersing device include ball mills, sand mills, ring mills, attritors, roll mills, agitators, Henschel mixers, colloid mills, ultrasonic homogenizers, pearl mills, wet jet mills, and paint shakers.

The dispersing agent is not particularly limited and may be appropriately selected depending on the intended purpose. Examples of the dispersing agent include polymer dispersing agents.

A volume average particle diameter of the pigment is not particularly limited and may be appropriately selected depending on the intended purpose, but it is preferably 0.005 µm or more but 0.5 µm or less, more preferably 0.01 µm or more but 0.45 µm or less, particularly preferably 0.015 µm or more but 0.4 µm or less. When the volume average particle diameter of the pigment is 0.005 µm or more but 0.5

µm or less, head nozzles can be prevented from clogging, and storage stability, transparency, and photocurability of the ink can be retained.

A mass ratio (dispersing agent/pigment) of the amount of the dispersing agent (% by mass) to the amount of the pigment (% by mass) is preferably 0.01 or more but 0.50 or less.

An amount of the colorant is preferably 0.5% by mass or more but 10% by mass or less, more preferably 1% by mass or more but 8% by mass or less, relative to the total amount of the active-energy-ray-curable composition.

Note that, an amount of a white pigment (e.g., titanium oxide) as a colorant in a white ink is preferably 5% by mass or more but 30% by mass or less, more preferably 10% by mass or more but 25% by mass or less, in order to achieve concealment.

—Photopolymerizable Compound Other than (Meth) Acrylic Acid Ester Compound Represented by General Formula (1)—

The active-energy-ray-curable composition may contain other photopolymerizable compounds than the (meth)acrylic acid ester compound represented by the General Formula (1).

The other photopolymerizable compounds than the (meth)acrylic acid ester compound represented by the General Formula (1) are not particularly limited and may be appropriately selected depending on the intended purpose. Example of the other photopolymerizable compounds than the (meth)acrylic acid ester compound represented by the General Formula (1) include photoradically polymerizable compounds, photocationically polymerizable compounds, and photoanionically polymerizable compounds. These may be used alone or in combination thereof.

The photoradically polymerizable compounds are not particularly limited and may be appropriately selected depending on the intended purpose so long as the photoradically polymerizable compounds are compounds containing one or more ethylenically unsaturated group(s) capable of polymerizing through light. Examples of the photoradically polymerizable compounds include monomers, oligomers, and polymers. These may be used alone or in combination thereof.

Examples of the photoradically polymerizable compounds include unsaturated carboxylic acids (e.g., acrylic acid, methacrylic acid, itaconic acid, crotonic acid, isocrotonic acid, and maleic acid), salts of the unsaturated carboxylic acids and compounds derived from the unsaturated carboxylic acids, anhydrides containing an ethylenically unsaturated group, acrylonitrile, styrene, unsaturated polyesters, unsaturated polyethers, unsaturated polyamides, and unsaturated polyurethanes. These may be used alone or in combination thereof.

Specific examples of the photoradically polymerizable compounds include: acrylic acid derivatives (e.g., 2-hydroxyethyl acrylate, butoxyethyl acrylate, carbitol acrylate, cyclohexyl acrylate, tetrahydrofurfuryl acrylate, benzyl acrylate, bis(4-acryloxy polyethoxyphenyl)propane, neopentylglycol diacrylate, ethoxylated neopentylglycol diacrylate, propoxylated neopentylglycol diacrylate, 1,6-hexanediol diacrylate, ethyleneglycol diacrylate, diethyleneglycol diacrylate, triethyleneglycol diacrylate, tetraethyleneglycol diacrylate, polyethyleneglycol diacrylate, propyleneglycol diacrylate, dipropyleneglycol diacrylate, tripropyleneglycol diacrylate, tetrapropyleneglycol diacrylate, polypropylene glycol diacrylate, pentaerythritol triacrylate, pentaerythritol tetraacrylate, dipentaerythritol tetraacrylate, trimethylolpropane triacrylate, tetramethylolmethane tetraacrylate, oligoester acrylate, and epoxy acrylate); methacrylic acid derivatives (e.g., methyl methacrylate, n-butyl methacrylate, allylmethacrylate, glycidyl methacrylate, benzyl methacrylate, dimethylaminomethyl methacrylate, 1,6-hexanediol dimethacrylate, ethylene glycol dimethacrylate, triethyleneglycol dimethacrylate, polyethylene glycol dimethacrylate, polypropylene glycol dimethacrylate, trimethylolethane trimethacrylate, trimethylolpropane trimethacrylate, and 2,2-bis(4-methacryloxypolyethoxyphenyl)propane); acrylamide derivatives (e.g., N-methylolacrylamide, diacetoneacrylamide, 2-hydroxyethylacrylamide, and acryloylmorpholine); derivatives of allyl compounds (e.g., allylglycidyl ether, diallyl phthalate, and triallyl trimellitate); divinyl ether compounds or trivinyl ether compounds (e.g., ethylene glycol divinyl ether, ethyleneglycolmonovinyl ether, diethylene glycol divinyl ether, triethyleneglycolmonovinyl ether, triethyleneglycoldivinyl ether, propyleneglycoldivinyl ether, dipropyleneglycoldivinyl ether, butanedioldivinyl ether, hexanediol divinyl ether, cyclohexanedimethanoldivinyl ether, hydroxyethylmonovinyl ether, hydroxynonylmonovinyl ether, and trimethylolpropanetrivinyl ether); monovinyl ether compounds (e.g., ethyl vinyl ether, n-butylvinyl ether, isobutylvinyl ether, octadecylvinyl ether, cyclohexylvinyl ether, hydroxybutylvinyl ether, 2-ethylhexylvinyl ether, cyclohexanedimethanolmonovinyl ether, n-propylvinyl ether, isopropylvinyl ether, isopropenyl ether-o-propylene carbonate, dodecylvinyl ether, diethyleneglycol monovinyl ether, and octadecylvinyl ether); 2-ethylhexylcliglycol acrylate, 2-hydroxy-3-phenoxy propyl acrylate, 2-hydroxybutyl acrylate, hydroxypivalic acid neopentylglycol diacrylate, 2-acryloyloxyethylphthalic acid, metoxypolyethyleneglycol acrylate, tetramethylolmethane triacrylate, 2-acryloyloxyethyl-2-hydroxyethylphthalic acid, dimethyloltricyclodecane diacrylate, ethoxylatedphenyl acrylate, 2-acryloyloxyethylsuccinic acid, nonylphenolethylene oxide adduct acrylate, modified glycerintriacrylate, bisphenol A diglycidyletheracrylic acid adducts, modified bisphenol A diacrylate, phenoxypolyethyleneglycol acrylate, 2-acryloyloxyethylhexahydrophthalic acid, propyleneoxide adduct diacrylate of bisphenol A, ethylene oxide adduct diacrylate of bisphenol A, dipentaerythritol hexaacrylate, pentaerythritol triacrylate, tolylene diisocyanate urethane prepolymer, lactone-modified flexible acrylate, butoxy ethylacrylate, propyleneglycoldiglycidyletheracrylic acid adducts, pentaerythritol triacrylate, hexamethylene diisocyanate urethane prepolymer, 2-hydroxy ethylacrylate, methoxydipropyleneglycol acrylate, ditrimethylolpropane tetraacrylate, pentaerythritol triacrylate, hexamethylene diisocyanate urethane prepolymer, stearyl acrylate, isoamyl acrylate, isomyristyl acrylate, isostearyl acrylate, and lactone-modified acrylate. These may be used alone or in combination thereof.

Examples of the photocationically polymerizable compounds include epoxy resins, vinyl ether compounds, and oxetane compounds. These may be used alone or in combination thereof.

Examples of the photoanionically polymerizable compounds include epoxy compounds, lactone compounds, acrylic compounds, and methacrylic compounds. Among them, acrylic compounds and methacrylic compounds that are exemplified as the photoradically polymerizable compounds are preferable.

Examples of combinations of the photopolymerizable compounds and the photopolymerization initiators include combinations of the photoradically polymerizable compounds and the photoradical polymerization initiators, combinations of the photocationically polymerizable compounds and the cationic photopolymerization initiators, and combinations of the photoanionically polymerizable compounds and the anionic photopolymerization initiators.

A mass ratio (other photopolymerizable compounds than the (meth)acrylic acid ester compound represented by the General Formula (1)/(meth)acrylic acid ester compound represented by the General Formula (1)) of the amount of the other photopolymerizable compounds than the (meth)acrylic acid ester compound represented by the General Formula (1) to the amount (% by mass) of the (meth)acrylic acid ester compound represented by General Formula (1) is preferably 0.01 or more but 100 or less, more preferably 0.1 or more but 50 or less.

A mass ratio [(photopolymerization initiator/photopolymerazable compound+colorant)] of an amount (% by mass) of the photopolymerization initiator to an amount (% by mass) of the photopolymerazable compound and the colorant is preferably 0.01 or more but 0.50 or less, more preferably 0.02 or more but 0.40 or less, particularly preferably 0.05 or more but 0.30 or less.

The active-energy-ray-curable composition of the present disclosure may further contain a sentisizer if necessary in order to facilitate decomposition of the photopolymerization initiator through irradiation of the active energy rays.

—Sensitizer—

The active-energy-ray-curable composition may contain a sensitizer in order to facilitate decomposition of the photopolymerization initiator through irradiation of the active energy rays.

The sensitizer absorbs active energy rays to be in an electronically excited state. Then, in this state, the sensitizer contacts the polymerization initiator, to facilitate chemical changes (decomposition, radical reaction, and generation of acids or bases) of the polymerization initiator through action such as transfer of electrons, transfer of energy, and generation of heat.

A mass ratio of an amount (% by mass) of the sensitizer to an amount (% by mass) of the photopolymerization initiator is preferably $5 \times 10^{-3}$ or more but 200 or less, more preferably 0.02 or more but 50 or less.

The sensitizer is not particularly limited and may be appropriately selected depending on the intended purpose. Examples of the sensitizer include sensitizing dyes having an absorption wavelength falling within a range of from 350 nm through 450 nm.

Examples of the sensitizing dyes include polynuclear aromatic compounds (e.g., pyrene, perylene, and triphenylene), xanthenes (e.g., fluorescein, eosin, erythrosine, Rhodamine B, and rose bengal), cyanines (e.g., thiacarbocyanine and oxacarbocyanine), merocyanines (e.g., merocyanine and carbomerocyanine), thiazines (e.g., thionin, methylene blue, and toluidine blue), acridines (e.g., acridine orange, chloroflavin, and acriflavin), anthraquinones (e.g., anthraquinone), squaryliums (e.g., squarylium), and coumarins (e.g., 7-diethylamino-4-methylcoumarin). These may be used alone or in combination thereof.

—Cosensitizer—

The cosensitizer can improve the sensitizing dyes in sensitivity to active energy rays, and can prevent the photopolymerizable compound from polymerizing through oxygen.

The cosensitizer is not particularly limited and may be appropriately selected depending on the intended purpose. Examples of the cosensitizers include: amine compounds such as triethanolamine, p-dimethylaminobenzoic acid ethyl ester, p-formyldimethylaniline, and p-methylthiodimethylaniline; and thiols and sulfides such as 2-mercaptobenzothiazole, 2-mercaptobenzoxazole, 2-mercaptobenzimidazole, 2-mercapto-4(3H)-quinazoline, and β-mercaptonaphthalene. These may be used alone or in combination thereof.

The surfactants are not particularly limited and may be appropriately selected depending on the intended purpose. Examples of the surfactants include higher fatty acid surfactants, silicone surfactants, and fluorine surfactants.

The active-energy-ray-curable composition of the present disclosure may further contain a polymerization inhibitor.

—Polymerization Inhibitor—

The active-energy-ray-curable composition can contain the polymerization inhibitor in order to improve storage property (storage stability) of the active-energy-ray-curable composition, and in order to prevent heads from clogging due to thermal polymerization in cases where the active-energy-ray-curable composition is heated to lower viscosity before ejection.

The polymerization inhibitor in the active-energy-ray-curable composition is not particularly limited and may be appropriately selected depending on the intended purpose. Examples of the polymerization inhibitor include hydroquinone, benzoquinone, p-methoxyphenol, TEMPO, TEMPOL, and cupferron complexes of aluminium. These may be used alone or in combination thereof.

An amount of the polymerization inhibitor is preferably 200 ppm or more but 20,000 ppm or less.

—Solvent—

The active-energy-ray-curable composition is cured by the active energy rays, and preferably does not contain a solvent. However, the active-energy-ray-curable composition may contain a solvent in order to improve adhesiveness between a recording medium and the ink after curing, so long as it does not adversely affect curing speed of the ink.

The solvent is not particularly limited and may be appropriately selected depending on the intended purpose. Examples of the solvent include organic solvents and water. These may be used alone or in combination thereof.

An amount of the solvent is preferably 0.1% by mass or more but 5% by mass or less, more preferably 0.1% by mass or more but 3% by mass or less, relative to the total amount of the active-energy-ray-curable composition.

The active-energy-ray-curable composition of the present disclosure may further contain a surfactant, a leveling additive, a matting agent, a polyester resin for adjusting membrane property, a polyurethane resin, a vinyl resin, an acrylic resin, a rubber resin, and wax.

Additionally, the active-energy-ray-curable composition of the present disclosure may further contain a tackifier that does not inhibit polymerization in order to improve adhesiveness to, for example, polyolefin films and PET.

<Active Energy Rays>

Active energy rays used for curing an active-energy-ray-curable composition of the present disclosure are not particularly limited, so long as they are able to give necessary energy for allowing polymerization reaction of polymerizable components in the composition to proceed. Examples of the active energy rays include electron beams, α-rays, β-rays, γ-rays, and X-rays, in addition to ultraviolet rays.

When a light source having a particularly high energy is used, polymerization reaction can be allowed to proceed without a polymerization initiator. In addition, in the case of irradiation with ultraviolet ray, mercury-free is preferred in terms of protection of environment. Therefore, replacement with GaN-based semiconductor ultraviolet light-emitting devices is preferred from industrial and environmental point of view. Furthermore, ultraviolet light-emitting diode (UV-LED) and ultraviolet laser diode (UV-LD) are preferable as an ultraviolet light source. Small sizes, long time working life, high efficiency, and high cost performance make such irradiation sources desirable.

<Preparation of Active-Energy-Ray-Curable Composition>

The active-energy-ray-curable composition of the present disclosure can be prepared by using the components described above. The preparation devices and conditions are not particularly limited. For example, the curable-composition can be prepared by subjecting a polymerizable monomer, a pigment, a dispersant, etc., to a dispersion treatment using a dispersing machine such as a ball mill, a kitty mill, a disk mill, a pin mill, and a DYNO-MILL to prepare a pigment liquid dispersion, and further mixing the pigment liquid dispersion with a polymerizable monomer, an initiator, a polymerization initiator, and a surfactant.

<Viscosity>

The viscosity of the active-energy-ray-curable composition of the present disclosure has no particular limit because it can be adjusted depending on the purpose and application devices. For example, if an ejecting device that ejects the composition from nozzles is employed, the viscosity thereof is preferably in the range of 3 mPa·s to 40 mPa·s, more preferably 5 mPa·s to 15 mPa·s, and particularly preferably 6 mPa·s to 12 mPa·s in the temperature range of 20 degrees C. to 65 degrees C., preferably at 25 degrees C. In addition, it is particularly preferable to satisfy this viscosity range by the composition free of the organic solvent described above. Incidentally, the viscosity can be measured by a cone plate rotary viscometer (VISCOMETER TVE-22L, manufactured by TOM SANGYO CO., LTD.) using a cone rotor (1°34'× R24) at a number of rotation of 50 rpm with a setting of the temperature of hemathermal circulating water in the range of 20 degrees C. to 65 degrees C. VISCOMATE VM-150III can be used for the temperature adjustment of the circulating water.

<Application Field>

The application field of the active-energy-ray-curable composition of the present disclosure is not particularly limited. It can be applied to any field where active-energy-ray-curable compositions are used. For example, the curable composition is selected to a particular application and used for a resin for processing, a paint, an adhesive, an insulant, a releasing agent, a coating material, a sealing material, various resists, various optical materials, and building materials such as walls and floors.

Figure 2:
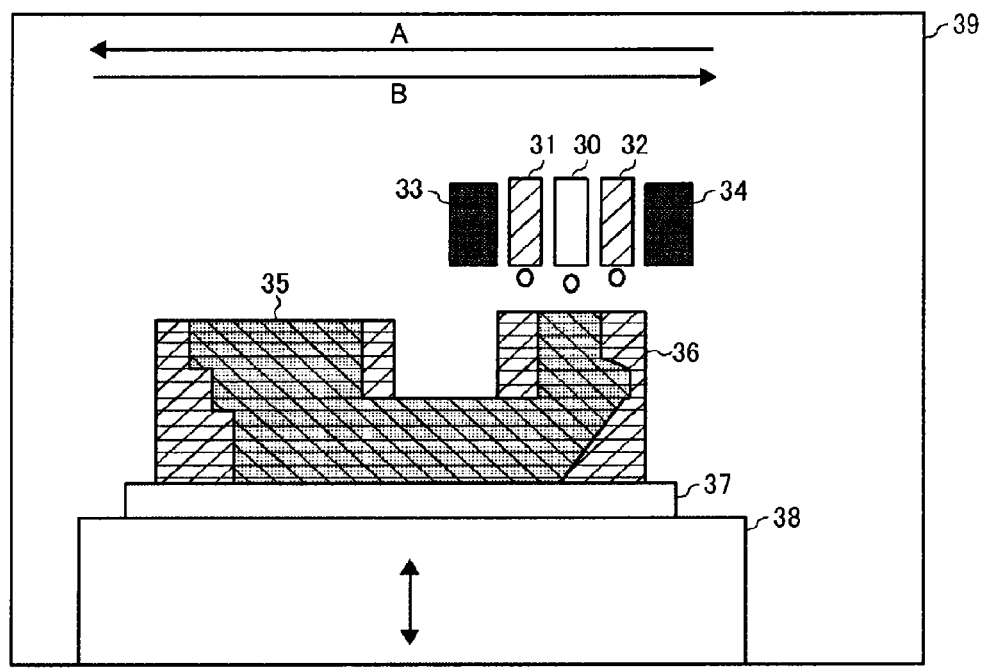
FIG. 2 is a schematic view of an example of another image forming apparatus of the present disclosure.
Figure 3A:
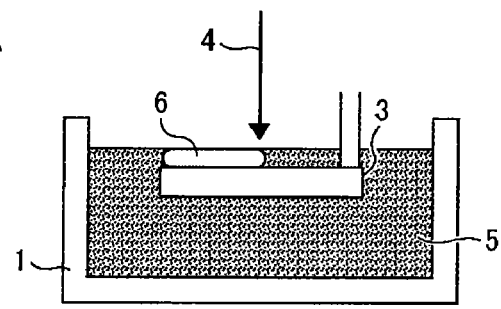
FIG. 3A is a schematic view of an example of still another image forming apparatus of the present disclosure.
Figure 3B:
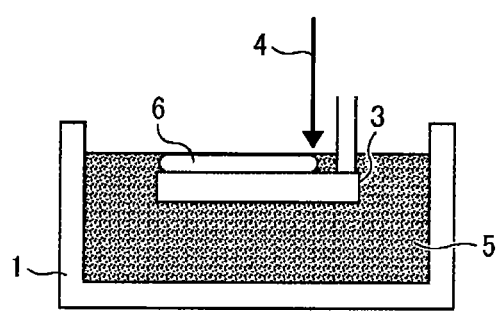
FIG. 3B is a schematic view of an example of still another image forming apparatus of the present disclosure.
Figure 3C:
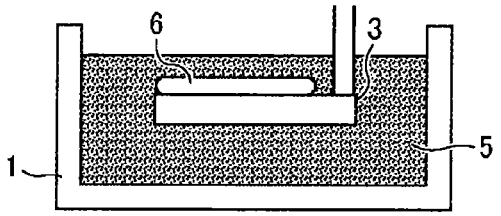
FIG. 3C is a schematic view of an example of still another image forming apparatus of the present disclosure.
Figure 3D:
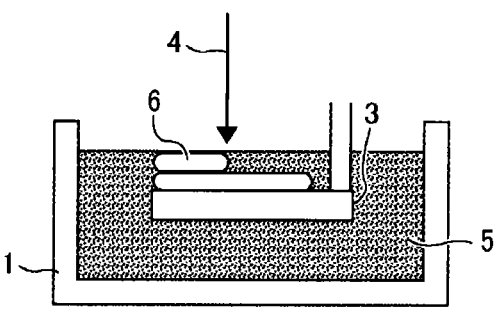
FIG. 3D is a schematic view of an example of still another image forming apparatus of the present disclosure.

Furthermore, the active-energy-ray-curable composition of the present disclosure can be used as an ink to form two-dimensional texts, images, and designed coating film on various substrates and in addition as a solid object forming material to form a three-dimensional object. This three dimensional object forming material may also be used as a binder for powder particles used in a powder layer laminating method of forming a three-dimensional object by repeating curing and layer-forming of powder layers, and as a three-dimensional object constituent material (a model material) and a supporting member used in an additive manufacturing method (a stereolithography method) as illustrated in FIG. 2, FIG. 3A, FIG. 3B, FIG. 3C, and FIG. 3D. FIG. 2 is a diagram illustrating a method of additive manufacturing to sequentially form layers of the active-energy-ray-curable composition of the present disclosure one on top of the other by repeating discharging the curable composition to particular areas followed by curing upon irradiation of an active energy ray. FIGS. 3A to 3D are each a diagram illustrating a method of additive manufacturing to sequentially form cured layers 6 having respective predetermined forms one on top of the other on a movable stage 3 by irradiating a storing pool (storing part) 1 of the active energy ray curable composition 5 of the present disclosure with the active energy ray 4.

An apparatus for fabricating a three-dimensional object by the active-energy-ray-curable composition of the present disclosure is not particularly limited and can be a known apparatus. For example, the apparatus includes a containing device, a supplying device, and a discharging device of the curable composition, and an active energy ray irradiator.

In addition, the present disclosure includes cured materials obtained by curing the active-energy-ray-curable composition and processed products obtained by processing structures having the cured materials on a substrate. The processed product is fabricated by, for example, heat-drawing and punching a cured material or structure having a sheet-like form or film-like form. Examples thereof are gauges or operation panels of vehicles, office machines, electric and electronic machines, and cameras.

The substrate is not particularly limited. It can suitably be selected to a particular application. Examples thereof include paper, thread, fiber, fabrics, leather, metal, plastic, glass, wood, ceramic, or composite materials thereof. Of these, plastic substrates are preferred in terms of processability.

<Ink Stored Container>

The ink stored container of the present disclosure contains the active-energy-ray-curable ink and is suitable for the applications as described above. For example, a container that stores the ink can be used as an ink cartridge or an ink bottle. Therefore, users can avoid direct contact with the ink during operations such as transfer or replacement of the ink, so that fingers and clothes are prevented from contamination. Furthermore, inclusion of foreign matters such as dust in the ink can be prevented. In addition, the container can be of any size, any form, and any material. For example, the container can be designed to a particular application. It is preferable to use a light blocking material to block the light or cover a container with a light blocking sheet, etc.

Next, the ink stored container will be described with reference to FIG. 4 and FIG. 5. Here, FIG. 4 is a view of one example of an ink stored container, and FIG. 5 is a view of the ink stored container 200 of FIG. 4 including a case (exterior housing) (the ink stored container is indicated by reference numerical 200 in FIG. 4).

Figure 4:
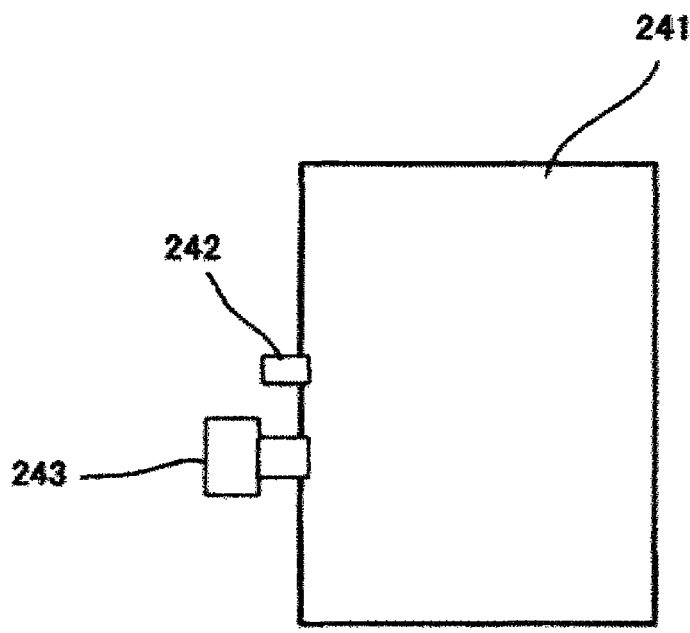
FIG. 4 is a schematic view of an example of an ink bag of an ink stored container.
Figure 5:
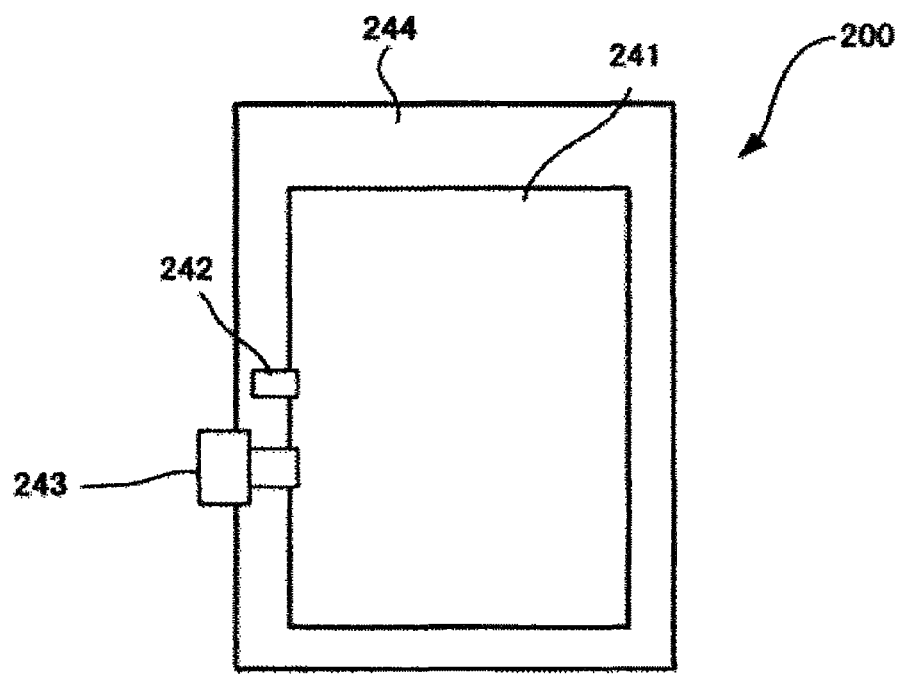
FIG. 5 is a schematic view of an example of an ink stored container containing an ink bag.

As illustrated in FIG. 4, in the ink stored container 200, an ink is inserted into an ink bag 241 from an ink inlet 242. After releasing air from the ink bag, the ink bag 241 is closed by fusing the ink inlet 242. At the time of use, a needle attached to the main body of the device is inserted into an ink outlet 243 formed of a rubber member to supply the ink to the device.

The ink bag 241 is formed of a wrapping member, such as an aluminium laminate film that cannot transmit air. As illustrated in FIG. 5, the ink bag 241 is typically housed in a plastic ink outlet case 244, which is detachably mounted on various devices.

(Ink Ejecting Device)

An ink ejecting device of the present disclosure includes the ink stored container of the present disclosure, and further includes other members if necessary.

<Image Forming Method and Image Forming Apparatus>

The image forming method of the present disclosure includes at least an irradiating step of irradiating the curable composition of the present disclosure with an active energy ray to cure the curable composition. The image forming apparatus of the present disclosure includes at least an irradiator to irradiate the curable composition of the present disclosure with an active energy ray and a storing part containing the active-energy-ray-curable composition of the present disclosure. The storing part may include the container mentioned above. Furthermore, the method and the apparatus may respectively include a discharging step and a discharging device to discharge the active energy ray curable composition. The method of discharging the curable composition is not particularly limited, and examples thereof include a continuous jetting method and an on-demand method. The on-demand method includes a piezo method, a thermal method, an electrostatic method, etc.

FIG. 1 is a diagram illustrating a two-dimensional image forming apparatus equipped with an inkjet discharging device. Printing units 23a, 23b, 23c, and 23d respectively having ink cartridges and discharging heads for yellow, magenta, cyan, and black active-energy-ray-curable inks discharge the inks onto a recording medium 22 fed from a supplying roller 21. Thereafter, light sources 24a, 24b, 24c, and 24d configured to cure the inks emit active energy rays to the inks, thereby curing the inks to form a color image. Thereafter, the recording medium 22 is conveyed to a processing unit 25 and a printed matter reeling roll 26. Each of the printing unit 23a, 23b, 23c and 23d may have a heating mechanism to liquidize the ink at the ink discharging portion. Moreover, in another embodiment of the present disclosure, a mechanism may optionally be included to cool down the recording medium to around room temperature in a contact or non-contact manner. In addition, the inkjet recording method may be either of serial methods or line methods. The serial methods include discharging an ink onto a recording medium by moving the head while the recording medium intermittently moves according to the width of a discharging head. The line methods include discharging an ink onto a recording medium from a discharging head held at a fixed position while the recording medium continuously moves.

The recording medium 22 is not particularly limited. Specific examples thereof include, but are not limited to, paper, film, metal, or complex materials thereof. The recording medium 22 takes a sheet-like form but is not limited thereto. The image forming apparatus may have a one-side printing configuration and/or a two-side printing configuration.

Optionally, multiple colors can be printed with no or weak active energy ray from the light sources 24a, 24b, and 24c followed by irradiation of the active energy ray from the light source 24d. As a result, energy and cost can be saved.

The recorded matter having images printed with the ink of the present disclosure includes articles having printed images or texts on a plain surface of conventional paper, resin film, etc., a rough surface, or a surface made of various materials such as metal or ceramic. In addition, by laminating layers of images in part or the entire of a recording medium, a partially stereoscopic image (formed of two dimensional part and three-dimensional part) and a three dimensional objects can be fabricated.

FIG. 2 is a schematic diagram illustrating another example of the image forming apparatus (apparatus to fabricate a 3D object) of the present disclosure. An image forming apparatus 39 illustrated in FIG. 2 sequentially forms thin layers one on top of the other using a head unit having inkjet heads arranged movable in the directions indicated by the arrows A and B. In the image forming apparatus 39, an ejection head unit 30 for additive manufacturing ejects a first active-energy-ray-curable composition, and ejection head units 31 and 32 for support and curing these compositions ejects a second active-energy-ray-curable composition having a different composition from the first active-energy-ray-curable composition, while ultraviolet irradiators 33 and 34 adjacent to the ejection head units 31 and 32 cure the compositions. To be more specific, for example, after the ejection head units 31 and 32 for support eject the second active-energy-ray-curable composition onto a substrate 37 for additive manufacturing and the second active-energy-ray-curable composition is solidified by irradiation of an active energy ray to form a first substrate layer having a space for composition, the ejection head unit 30 for additive manufacturing ejects the first active-energy-ray-curable composition onto the pool followed by irradiation of an active energy ray for solidification, thereby forming a first additive manufacturing layer. This step is repeated multiple times lowering the stage 38 movable in the vertical direction to laminate the supporting layer and the additive manufacturing layer to fabricate a solid object 35. Thereafter, an additive manufacturing support 36 is removed, if desired. Although only a single ejection head unit 30 for additive manufacturing is provided to the image forming apparatus illustrated 39 in FIG. 2, it can have two or more units 30.

EXAMPLES

The present disclosure will be described by way of the following Examples. However, the present disclosure should not be construed as being limited to these Examples.

$^1$H-NMR spectra were measured using $^1$H-NMR (500 MHz) (ECX500, available from JEOL Ltd.), and IR spectra were measured using FT-IR Spectrum GX (SPECTRUM GX, available from PERKIN ELMER).

Example 1a

The following procedure was performed to synthesize compound 1a.

DL ethyl mandelate (12.6 g, 70 mmol) (available from Tokyo Chemical Industry Co., Ltd.) was added to dehydrated dichloromethane (130 mL) in a flask, and the flask was purged with argon gas. Then, triethylamine (8.5 g, 84 mmol) was added to the flask. The resultant mixture was cooled to about −10° C., and acrylic chloride (7.6 g, 84 mmol) was slowly added dropwise thereto so that a system temperature would be in a range of from −10° C. through −5° C. Then, the resultant mixture was stirred for 2 hours at room temperature. The precipitate was removed through filtration, and the thus-obtained filtrate was washed with water, a saturated sodium hydrogencarbonate aqueous solution, and a saturated sodium chloride aqueous solution. The filtrate was dried with sodium sulfate, and was concentrated under reduced pressure to obtain a oily brown product. A column was loaded with WAKOGEL C300 (available from Wako Pure Chemical Industries, Ltd.) (350 g), and the oily brown product was purified by column chromatography using hexane and ethyl acetate as eluents to obtain an oily colorless product of compound (1a) represented by the following chemical formula (11.2 g, yield: about 68%).

Compound (1a)

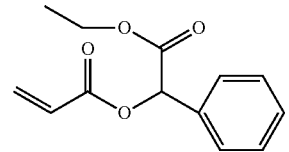

Identification data of the compound (1a) are as follows.
$^1$H-NMR (CDCl$_3$):δ1.22(t, 3H), 4.10-4.27(m, 2H), 5.94 (dd, 1H), 5.99(s, 1H), 6.22-6.28(m, 1H), 6.53(dd, 1H), 7.38-7.42 (m, 3H), 7.48-7.51(m, 2H)
IR(NaCl): 3067, 3037, 2984, 1754, 1732, 1635, 1498, 1456, 1407, 1371, 1335, 1296, 1259, 1214, 1174, 1083, 1045, 1029, 983, 925, 854, 808, 734, 698 cm$^{-1}$ Example 2a The following procedure was performed to synthesize compound 2a.

DL ethyl mandelate (10.8 g, 60 mmol) (available from Tokyo Chemical Industry Co., Ltd.) was added to dehydrated dichloromethane (130 mL) in a flask, and the flask was purged with argon gas. Then, triethylamine (7.3 g, 72 mmol) was added to the flask. The resultant mixture was cooled to about −10° C., and methacrylic chloride (7.5 g, 72 mmol) was slowly added dropwise thereto so that a system temperature would be in a range of from −10° C. through −5° C. Then, the resultant mixture was stirred for 2 hours at room temperature. The precipitate was removed through filtration, and the thus-obtained filtrate was washed with water, a saturated sodium hydrogencarbonate aqueous solution, and a saturated sodium chloride aqueous solution. The filtrate was dried with sodium sulfate, and was concentrated under reduced pressure to obtain a oily brown product. A column was loaded with WAKOGEL C300 (available from Wako Pure Chemical Industries, Ltd.) (300 g), and the oily brown product was purified by column chromatography using hexane and ethyl acetate as eluents to obtain an oily colorless product of compound (2a) represented by the following chemical formula (8.0 g, yield: about 54%).

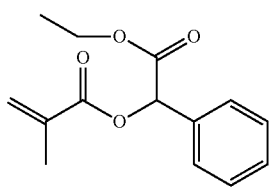

Compound (2a)

Identification data of the compound (2a) are as follows.
$^1$H-NMR (CDCl$_3$):δ1.22(t, 3H), 1.60, 1.63, 2.01 (s, 3H), 1.66, 1.73(s, 1H), 4.10-4.26(m, 2H), 5.66-5.68, 5.94-5.96, 6.26-6.28(m, 2H)
IR(NaCl): 3036, 2985, 2935, 1754, 1725, 1680, 1637, 1498, 1455, 1371, 1323, 1294, 1268, 1243, 1213, 1154, 1109, 1042, 949, 856, 813, 763, 732, 697, 603, 544 cm$^{-1}$ Example 3a The following procedure was performed to synthesize compound 3a.

DL methyl mandelate (11.6 g, 70 mmol) (available from Tokyo Chemical Industry Co., Ltd.) was added to dehydrated dichloromethane (130 mL) in a flask, and the flask was purged with argon gas. Then, triethylamine (8.5 g, 84 mmol) was added to the flask. The resultant mixture was cooled to about −10° C., and acrylic chloride (7.6 g, 84 mmol) was slowly added dropwise thereto so that a system temperature would be in a range of from −10° C. through −5° C. Then, the resultant mixture was stirred for 2 hours at room temperature. The precipitate was removed through filtration, and the thus-obtained filtrate was washed with water, a saturated sodium hydrogencarbonate aqueous solution, and a saturated sodium chloride aqueous solution. The filtrate was dried with sodium sulfate, and was concentrated under reduced pressure to obtain a oily brown product. A column was loaded with WAKOGEL C300 (available from Wako Pure Chemical Industries, Ltd.) (300 g), and the oily brown product was purified by column chromatography using hexane and ethyl acetate as eluents to obtain an oily colorless product of compound (3a) represented by the following chemical formula (11.1 g, yield: about 72%).

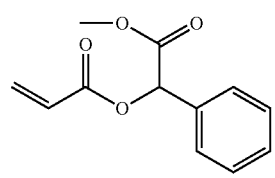

Compound (3a)

Identification data of the compound (3a) are as follows.
$^1$H-NMR(CDCl$_3$):δ3.74(s, 3H), 5.94(dd, 1H), 6.02(s, 1H), 6.23-6.28(m, 1H), 6.54(dd, 1H), 7.38-7.42(m, 3H), 7.48-7.51(m, 2H)
IR(NaCl): 3067, 3037, 2956, 1758, 1731, 1634, 1619, 1588, 1498, 1455, 1437, 1407, 1352, 1275, 1258, 1219, 1171, 1083, 1065, 1016, 980, 937, 854, 809, 782, 735, 698, 677, 650, 549 cm$^{-1}$ Example 4a The following procedure was performed to synthesize compound 4a.

DL benzyl mandelate (13.3 g, 55 mmol) (available from Tokyo Chemical Industry Co., Ltd.) was added to dehydrated dichloromethane (130 mL) in a flask, and the flask was purged with argon gas. Then, trimethylamine (6.7 g, 66 mmol) was added to the flask. The resultant mixture was cooled to about −10° C., and acrylic chloride (6.0 g, 66 mmol) was slowly added dropwise thereto so that a system temperature would be in a range of from −10° C. through −5° C. Then, the resultant mixture was stirred for 2 hours at room temperature. The precipitate was removed through filtration, and the thus-obtained filtrate was washed with water, a saturated sodium hydrogencarbonate aqueous solution, and a saturated sodium chloride aqueous solution. The filtrate was dried with sodium sulfate, and was concentrated under reduced pressure to obtain a oily brown product. A column was loaded with WAKOGEL C300 (available from Wako Pure Chemical Industries, Ltd.) (300 g), and the oily brown product was purified by column chromatography using hexane and ethyl acetate as eluents to obtain an oily colorless product of compound (4a) represented by the following chemical formula (12.5 g, yield: about 77%).

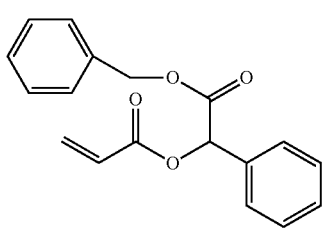

Compound (4a)

Identification data of the compound (4a) are as follows.
$^1$H-NMR (CDCl$_3$):δ5.14(d, 1H), 5.20(d, 1H), 5.93(dd, 1H), 6.06(s, 1H), 6.22-6.28(m, 1H), 6.53(dd, 1H), 7.19-7.22(m, 2H), 7.28-7.31(m, 3H), 7.37-7.40(m, 3H), 7.46-7.50(m, 2H)
IR(NaCl): 3066, 3035, 2957, 1756, 1731, 1634, 1618, 1587, 1498, 1456, 1406, 1379, 1333, 1258, 1208, 1169, 1083, 1064, 1029, 1003, 982, 849, 808, 778, 737, 697, 589, 546, 500 cm$^{-1}$ Example 5a The following procedure was performed to synthesize compound 5a.
Mandelonitrile (9.3 g, 70 mmol) (available from COMBI-BLOCKS) was added to dehydrated dichloromethane (130 mL) in a flask, and the flask was purged with argon gas. Then, triethylamine (8.5 g, 84 mmol) was added to the flask. The resultant mixture was cooled to about −10° C., and acrylic chloride (7.6 g, 84 mmol) was slowly added dropwise thereto so that a system temperature would be in a range of from −10° C. through −5° C. Then, the resultant mixture was stirred for 2 hours at room temperature. The precipitate was removed through filtration, and the thus-obtained filtrate was washed with water, a saturated sodium hydrogencarbonate aqueous solution, and a saturated sodium chloride aqueous solution. The filtrate was dried with sodium sulfate, and was concentrated under reduced pressure to obtain an oily yellow product. A column was loaded with WAKOGEL C300 (available from Wako Pure Chemical Industries, Ltd.) (350 g), and the oily yellow product was purified by column chromatography using hexane and ethyl acetate as eluents to obtain an oily colorless product of compound (5a) represented by the following chemical formula (9.1 g, yield: about 69%).

Compound (5a)

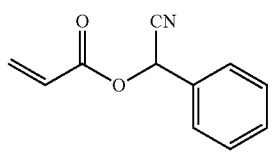

Identification data of the compound (5a) are as follows.
$^1$H-NMR(CDCl$_3$):δ6.00(dd, 1H), 6.15-6.20 (m, 1H), 6.51 (s, 1H), 6.55(dd, 1H), 7.45-7.48(m, 3H), 7.53-7.56(m, 2H)
IR(NaCl): 3069, 3039, 2950, 1738, 1633, 1496, 1457, 1406, 1294, 1247, 1163, 1039, 983, 956, 923, 901, 828, 805, 760, 697, 622, 523 cm$^{-1}$ Comparative Example 1a A commercially available product of phenoxyethyl acrylate represented by the following chemical formula (available from Tokyo Chemical Industry Co., Ltd.) was used as a compound of Comparative Example 1a (Comparative Compound 1a).

Compound (Comparative Compound 1a)

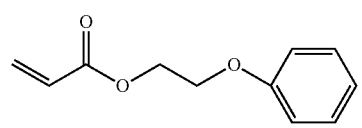

Comparative Example 2a

A commercially available product of isobornyl acrylate represented by the following chemical formula (available from Tokyo Chemical Industry Co., Ltd.) was used as a compound of Comparative Example 2a (Comparative Compound 2a).

Compound (Comparative Compound 2a)

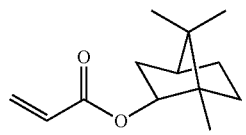

Comparative Example 3a

A compound represented by the following chemical formula, which had been synthesized according to Synthesis Example 5 described in Japanese Unexamined Patent Application Publication No. 2013-256487, was used as a compound of Comparative Example 3a (Comparative Compound 3a).

Compound (Comparative Compound 3a)

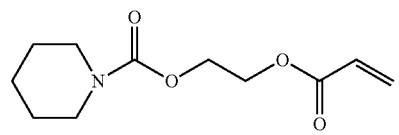

Comparative Example 4a

A compound represented by the following chemical formula, which had been synthesized according to Synthesis Example 7 described in Japanese Unexamined Patent Application Publication No. 2013-256487, was used as a compound of Comparative Example 4a (Comparative Compound 4a).

Compound (Comparative Compound 4a)

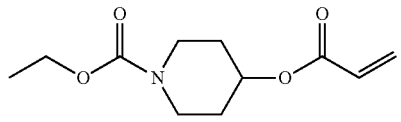

Comparative Example 5a

A commercially available product of ethylene glycol phenyl ether methacrylate (phenoxyethyl methacrylate) represented by the following chemical formula (available from Sigma-Aldrich) was used as a compound of Comparative Example 5a (Comparative Compound 5a).

Compound (Comparative Compound 5a)

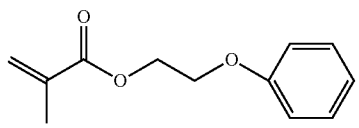

Active-energy-ray-curable compounds of the compounds 1a to 5a and the Comparative Compounds 1a to 5a were each evaluated for viscosity and presence or absence of odor in the following manners. Results are presented in Table 1.

<Viscosity>

A cone plate rotary viscometer, VISCOMETER TVE-22L (available from Toki Sangyo Co., Ltd) was used to measure viscosity of each of the active-energy-ray-curable compounds of the compounds 1a to 5a and Comparative Compounds 1a to 5a with a cone rotor (1°34'×R24) under the following conditions (number of rotations: 50 rpm, temperature of thermostatic circulating water: 25° C.).

<Presence or Absence of Odor>

The active-energy-ray-curable compounds of the compounds 1a to 5a and Comparative Compounds 1a to 5a were each evaluated for "presence or absence of odor" according to the following procedures (1) to (3). Evaluation criteria are as follows.

(1) About 100 mg (about 0.1 g) of each of the compounds was weighed in a sample bottle (glass bottle) (50 mL) and the sample bottle was closed with a cap.
(2) The sample bottle was left to stand for about 30 minutes at room temperature.
(3) Odor given off upon opening the cap of the sample bottle (glass bottle) was smelled by putting the nose close to the sample bottle.

[Evaluation Criteria]

A: There was no perceivable odor, or there was odor that does not cause uncomfortable feeling.
B: Peculiar odor causes uncomfortable feeling.
C: Peculiar odor causes strong uncomfortable feeling.

TABLE 1

|  |  | Active-energy-ray-curable composition | Viscosity (25° C., mPa · s) | Presence or Absence of odor |
|---|---|---|---|---|
| Example | 1a | Compound (1a) | 25.1 | A |
|  | 2a | Compound (2a) | 78.0 | A |
|  | 3a | Compound (3a) | 57.2 | A |
|  | 4a | Compound (4a) | 112.4 | A |
|  | 5a | Compound (5a) | 11.6 | B |
| Comparative Example | 1a | Phenoxyethyl acrylate | 10.4 | C |
|  | 2a | Isobornyl acrylate | 10.7 | C |
|  | 3a | Compound of Synthesis Example 5 described in Japanese Unexamined Patent Application No. 2013-256487 | 11.7 | A |
|  | 4a | Compound of Synthesis Example 7 described in Japanese Unexamined Patent Application No. 2013-256487 | 28.8 | A |
|  | 5a | Phenoxyethyl methacrylate | 22.5 | C |

As described in Table 1, it was found that the active-energy-ray-curable compounds of Examples 1a to 5a, and Comparative Examples 3a and 4a have little odor. In Examples 1a to 5a, it was found that the active-energy-ray-curable compounds of Examples 1a to 4a have particularly considerably little odor.

Examples 1b to 5b

—Preparation of Photocurable Composition—

Each (950 mg) of the active-energy-ray-curable compounds (compounds 1a to 5a) of Examples 1a to 5a, and the photopolymerization initiator (50 mg) (product name: IRGACURE 907, component name: 2-methy-1-[4-(methylthio)phenyl]-2-morpholinopropan-1-one, available from BASF Japan Ltd.) were mixed together using a magnetic stirrer to prepare active-energy-ray-curable compositions A to E of Examples 1b to 5b.

Comparative Example 1b to Comparative Example 5b

Active-energy-ray-curable compositions F to J of Comparative Examples 1b to 5b were prepared in the same manners as in Example 1b except that the active-energy-ray-curable compound of Example 1a was changed to each of the active-energy-ray-curable compounds presented in Table 2.

Next, the active-energy-ray-curable compositions A to J of the Examples 1b to 5b and Comparative Examples 1b to 5b were each evaluated for photopolymerizing ability and photocurability in the following manners. Results are presented in Table 2.

<Photopolymerizing Ability>

A differential scanning calorimeter (product name: DSC-7020, available from Seiko Instruments Inc.) and an ultraviolet ray irradiating device (PDC-7, available from Hitachi High-Tech Science Corporation) were used to evaluate the active-energy-ray-curable composition for photopolymerizing ability.

Specifically, one sample was measured twice for an amount of heat generated in the case where the active-energy-ray-polymerizable compound was irradiated with ultraviolet rays having a wavelength of 365 nm at 200 mW/cm$^2$ for a sufficient time to terminate polymerization of the active-energy-ray-polymerizable compound.

The amount of heat generated in the first measurement includes not only an amount of heat generated through polymerization of the active-energy-ray-polymerizable compound but also an amount of heat generated through ultraviolet irradiation. Therefore, the sample that had undergone polymerization in the first measurement was irradiated again with ultraviolet rays under the same conditions described above, to measure an amount of heat generated other than the amount of heat generated through polymerization of the active-energy-ray-polymerizable compound. Then, the amount of heat generated through polymerization of the active-energy-ray-polymerizable compound was calculated based on a difference between the amount of heat generated in the first measurement and the amount of heat generated in the second measurement. Here, the time for attaining a maximum amount of heat generated from the start of ultraviolet rays irradiation was defined as "$T_1$ [s]", which was used as an indicator of comparison of speeds of photopolymerization.

<Photocurability>

A viscoelasticity measuring apparatus (product name: MCR302, available from Anton-Parr) with a measuring cell for UV curing as an option and a LED light source (product name: LIGHTNINGCURE LC-L1, available from Hamamatsu Photonics K. K.) were used to measure each of the active-energy-ray-curable compositions for photocurability.

Specifically, using a cone plate having a diameter of 20 mm, a sample was put into a gap of 10 μm, and then was irradiated with ultraviolet rays having a wavelength of 365 nm at 50 mW/cm². Then, change of viscoelasticity was measured until the elastic modulus of the sample was saturated. A maximum value of the elastic modulus was determined based on the measurement results, and was used for an indicator of the curing level.

Moreover, energy of ultraviolet rays (that is, curing energy), which was irradiated until the elastic modulus was saturated, was calculated by multiplying intensity of ultraviolet rays (50 mW/cm²) by time [s] for which the ultraviolet rays were emitted.

TABLE 2

|  |  | Active-energy-ray-curable composition | Photopoly-merizing ability $T_1$ (second) | Photocurability | |
|---|---|---|---|---|---|
|  |  |  |  | Storage modulus (Pa) | Curing energy (mJ/cm²) |
| Example | 1b | A | 2.4 | $4.0 \times 10^5$ | 50 |
|  | 2b | B | 6.0 | $1.2 \times 10^5$ | 980 |
|  | 3b | C | 2.4 | $5.3 \times 10^5$ | 68 |
|  | 4b | D | 2.4 | $3.2 \times 10^5$ | 55 |
|  | 5b | E | 2.4 | $2.0 \times 10^5$ | 70 |
| Comparative | 1b | F | 2.5 | $4.8 \times 10^4$ | 200 |
| Example | 2b | G | 3.0 | $1.0 \times 10^5$ | 104 |
|  | 3b | H | 4.5 | $5.0 \times 10^4$ | 380 |
|  | 4b | I | 3.2 | $8.4 \times 10^4$ | 150 |
|  | 5b | J | 19.3 | $1.0 \times 10^5$ | 1257 |

From results of Table 2, it was found that the active-energy-ray-curable compositions of Examples 1b to 5b are excellent in photopolymerizing ability and photocurability. Particularly, it was found that the active-energy-ray-curable compositions of Examples have higher storage modulus and much lower curing energy than the active-energy-ray-curable compositions of Comparative Examples.

It was found that the active-energy-ray-curable compositions of Examples are more excellent in photocurability than the active-energy-ray-curable compositions of Comparative Examples 1b and 5b, each having a benzene ring similar to the active-energy-ray-curable compositions of Examples, and than the active-energy-ray-curable composition of Comparative Example 2b having an alicyclic structure. Therefore, introduction of a branched polar group (ester structure) imparts excellent functions to the active-energy-ray-curable composition. Moreover, it was found that the active-energy-ray-curable compositions of Examples have more excellent functions than the active-energy-ray-curable compositions of Comparative Examples 3b and 4b, which are obtained by introducing a alicyclic structure and a polar group to molecules thereof. This means that introduction of an aromatic ring structure and a branched polar group attains excellent effects of the active-energy-ray-curable compositions.

Example 1c to 5c

—Preparation of Ink—

Each (100 parts by mass) of the active-energy-ray-curable compounds (compounds 1a to 5a), which was obtained in Examples 1a to 5a, a photopolymerization initiator (10 parts by mass) (product name: IRGACURE 907, available from BASF Japan Ltd.), and carbon black (3 parts by mass) (product name: MICROLITH Black C-K, available from BASF Japan Ltd.) were mixed together to obtain inks of Examples 1c to 5c.

<Evaluation 1 of Curing Ability of Ink>

An inkjet recording apparatus (available from RICOH Company, Ltd., head: GEN4, available from Ricoh Printing Systems, Ltd.) was used to eject each of the inks of Examples 1c to 5c on a glass slide. Then, an UV irradiating device (product name: LH6, available from Fusion Systems Japan) was used to irradiate each ink with ultraviolet rays having a wavelength of 365 nm at 200 mW/cm² to cure the ink.

As a result, each of the inks could be ejected without problems, and the image formed with the ink could be sufficiently cured.

These inks substantially correspond to the inks containing the active-energy-ray-curable compositions of Examples 1b to 5b. Just in case, when photopolymerizing ability and curability of the inks were measured in the same manners as in the measurements of the active-energy-ray-curable compositions, all of the inks were excellent in photopolymerizing ability and curability, similar to the active-energy-ray-curable compositions of Examples 1b to 5b.

<Evaluation 2 of Curing Ability of Ink>

A nib of a pen was immersed in each of the inks of Examples 1c to 5c, and was used to write characters on a PET film and plain paper. Then, an UV irradiating device (product name: LH6, available from Fusion Systems Japan) was used to irradiate the ink with ultraviolet rays having a wavelength of 365 nm at 200 mW/cm² to cure the ink. As a result, the image formed with the ink could be sufficiently cured.

Aspects of the present disclosure are as follows.

<1> an Active-Energy-Ray-Curable Composition Including a (meth)acrylic acid ester compound represented by General Formula (1) below,

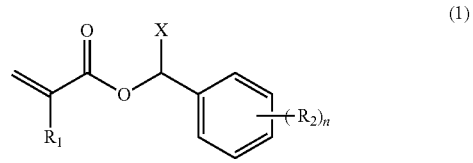

where in the General Formula (1), $R_1$ represents a hydrogen atom or a methyl group, $R_2$ represents a hydrogen atom, an alkyl group having from 1 through 5 carbon atoms, or an alkyloxy group having from 1 through 5 carbon atoms, n is an integer of from 0 through 5, and X represents an electron-withdrawing functional group.

<2> The active-energy-ray-curable composition according to <1>, wherein X in the General Formula (1) includes a structure containing a carbonyl group.

<3> The active-energy-ray-curable composition according to <1> or <2>, wherein the (meth)acrylic acid ester compound represented by the General Formula (1) includes a compound represented by General Formula (2) below,

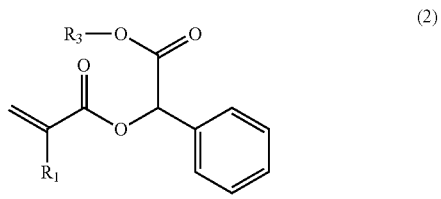

where in the General Formula (2), $R_1$ represents a hydrogen atom or a methyl group, $R_3$ represents a group selected from the group consisting of an aliphatic hydrocarbon group having from 1 through 10 carbon atoms, an alicyclic hydrocarbon group, and an aromatic hydrocarbon group.

<4> The active-energy-ray-curable composition according to <3>, wherein $R^3$ in the General Formula (2) represents an alkyl group having from 1 through 3 carbon atoms.

<5> The active-energy-ray-curable composition according to <3> or <4>, wherein the (meth)acrylic acid ester compound represented by the General Formula (2) includes a compound represented by General Formula (3) below,

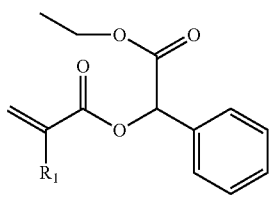

(3)

where in the General Formula (3), $R_1$ represents a hydrogen atom or a methyl group.

<6> The active-energy-ray-curable composition according to <5>, wherein $R^1$ in the General Formula (3) is a hydrogen atom.

<7> The active-energy-ray-curable composition according to any one of <1> to <6>, wherein the active-energy-ray-curable composition is a material for forming a three-dimensional object.

<8> An active-energy-ray-curable ink including a (meth)acrylic acid ester compound represented by General Formula (1) below,

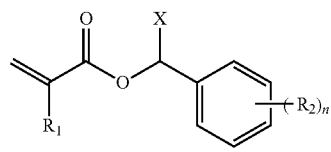

(1)

where in the General Formula (1), $R_1$ represents a hydrogen atom or a methyl group, $R_2$ represents a hydrogen atom, an alkyl group having from 1 through 5 carbon atoms, and an alkyloxy group having from 1 through 5 carbon atoms, n is an integer of from 0 through 5, and X represents an electron-withdrawing functional group.

<9> The active-energy-ray-curable ink according to <8>, wherein the active-energy-ray-curable ink is for inkjet.

<10> An ink stored container including;
a container; and
the active-energy-ray-curable ink according to <8> or <9> in the container.

<11> An ink ejecting device including the ink stored container according to <10>.

<12> A method for forming an image, the method including forming a two-dimensional or three-dimensional image with the active-energy-ray-curable composition according to any one of <1> to <7>.

<13> An image, which is formed with the active-energy-ray-curable composition according to any one of <1> to <7>.

<14> An active-energy-ray-curable compound, which is represented by any one of General Formulas (1) to (3) below,

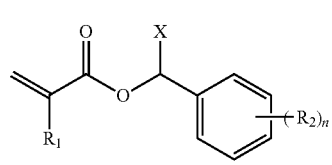

(1)

where in the General Formula (1), $R_1$ represents a hydrogen atom or a methyl group, $R_2$ represents a hydrogen atom, an alkyl group having from 1 through 5 carbon atoms, or an alkyloxy group having from 1 through 5 carbon atoms, n is an integer of from 0 through 5, and X represents an electron-withdrawing functional group,

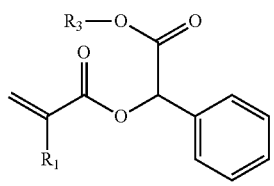

(2)

where in the General Formula (2), $R_1$ represents a hydrogen atom or a methyl group, $R_3$ represents a group selected from the group consisting of an aliphatic hydrocarbon group having from 1 through 10 carbon atoms, an alicyclic hydrocarbon group, and an aromatic hydrocarbon group,

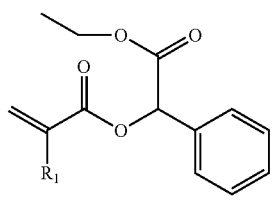

(3)

where in the General Formula (3), $R_1$ represents a hydrogen atom or a methyl group.

The active-energy-ray-curable composition according to any one of <1> to <7>, the active-energy-ray-curable ink according to <8> or <9>, the ink stored container according to <10>, the ink ejecting device according to <11>, the method for forming an image according to <12>, the image according to <13>, and the active-energy-ray-curable compound according to <14> can solve the existing problems, and can achieve the object of the present disclosure.

What is claimed is:

1. An active-energy-ray-curable composition, comprising:
a compound represented by the Formula (2):

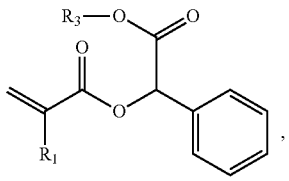
(2)

wherein
R$_1$ represents a hydrogen atom or a methyl group, and
R$_3$ represents a group selected from the group consisting of an aliphatic hydrocarbon group having from 1 through 10 carbon atoms, an alicyclic hydrocarbon group, and an aromatic hydrocarbon group.

2. The active-energy-ray-curable composition according to claim 1, wherein R$^3$ in the Formula (2) represents an alkyl group having from 1 through 3 carbon atoms.

3. The active-energy-ray-curable composition according to claim 1, wherein the (meth)acrylic acid ester compound represented by the Formula (2) comprises a compound represented by the Formula (3):

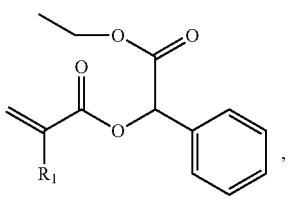
(3)

wherein R$_1$ represents a hydrogen atom or a methyl group.

4. The active-energy-ray-curable composition according to claim 3, wherein R$^1$ in the Formula (3) is a hydrogen atom.

5. The active-energy-ray-curable composition according to claim 1, wherein the active-energy-ray-curable composition is a material for forming a three-dimensional object.

6. An active-energy-ray-curable ink, comprising:
a compound represented by the Formula (2):

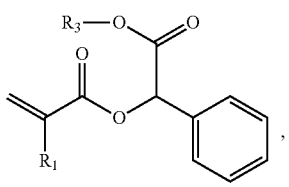
(2)

wherein
R$_1$ represents a hydrogen atom or a methyl group, and
R$_3$ represents a group selected from the group consisting of an aliphatic hydrocarbon group having from 1 through 10 carbon atoms, an alicyclic hydrocarbon group, and an aromatic hydrocarbon group.

7. The active-energy-ray-curable ink according to claim 6, wherein the active-energy-ray-curable ink is for inkjet.

8. An ink stored container comprising:
a container; and
the active-energy-ray-curable ink according to claim 6 in the container.

9. An ink ejecting device comprising
the ink stored container according to claim 8.

10. A method for forming an image, the method comprising forming a two-dimensional or three-dimensional image with the active-energy-ray-curable composition according to claim 1.

11. An image, which is formed with the active-energy-ray-curable composition according to claim 1.

12. An active-energy-ray-curable composition comprising a (meth)acrylic acid ester compound represented by the Formula (I'):

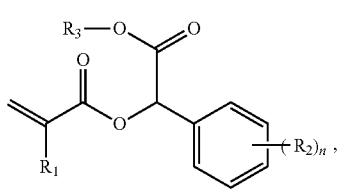
(I')

wherein
R$_1$ represents a hydrogen atom or a methyl group,
R$_2$ represents a hydrogen atom, an alkyl group having from 1 through 5 carbon atoms, or an alkyloxy group having from 1 through 5 carbon atoms, n is an integer of from 0 through 5, and
R$_3$ represents a group selected from the group consisting of an aliphatic hydrocarbon group having from 1 through 10 carbon atoms, an alicyclic hydrocarbon group, and an aromatic hydrocarbon group.

13. An active-energy-ray-curable ink, comprising:
a (meth)acrylic acid ester compound represented by the Formula (I'):

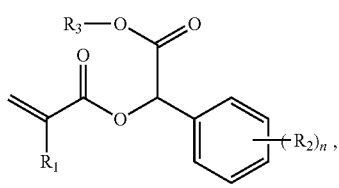
(I')

wherein
R$_1$ represents a hydrogen atom or a methyl group,
R$_2$ represents a hydrogen atom, an alkyl group having from 1 through 5 carbon atoms, or an alkyloxy group having from 1 through 5 carbon atoms, n is an integer of from 0 through 5, and.
R$_3$ represents a group selected from the group consisting of an aliphatic hydrocarbon group having from 1 through 10 carbon atoms, an alicyclic hydrocarbon group, and an aromatic hydrocarbon group.

* * * * *